(12) United States Patent
Throckmorton et al.

(10) Patent No.: US 9,919,085 B2
(45) Date of Patent: Mar. 20, 2018

(54) DUAL-PUMP CONTINUOUS-FLOW TOTAL ARTIFICIAL HEART

(71) Applicant: Drexel University, Philadelphia, PA (US)

(72) Inventors: Amy L Throckmorton, Cherry Hill, NJ (US); Carson S Fox, Philadelphia, PA (US); Steven G Chopski, Vinton, VA (US)

(73) Assignee: Drexel University, Philadelphia, PA (US)

( * ) Notice: Subject to any disclaimer, the term of this patent is extended or adjusted under 35 U.S.C. 154(b) by 65 days.

(21) Appl. No.: 15/058,888

(22) Filed: Mar. 2, 2016

(65) Prior Publication Data

US 2016/0256619 A1    Sep. 8, 2016

Related U.S. Application Data

(60) Provisional application No. 62/127,316, filed on Mar. 3, 2015.

(51) Int. Cl.
*A61M 1/10* (2006.01)
*A61M 1/16* (2006.01)
*A61M 1/12* (2006.01)

(52) U.S. Cl.
CPC ........ *A61M 1/1006* (2014.02); *A61M 1/1015* (2014.02); *A61M 1/1029* (2014.02); *A61M 1/1698* (2013.01); *A61M 1/122* (2014.02); *A61M 2205/3584* (2013.01)

(58) Field of Classification Search
CPC .. A61M 1/1006; A61M 1/1015; A61M 1/101; A61M 1/122; A61M 1/1698; A61M 1/1084
See application file for complete search history.

(56) References Cited

U.S. PATENT DOCUMENTS

| | | | |
|---|---|---|---|
| 5,300,111 | A | 4/1994 | Panton et al. |
| 8,210,829 | B2 | 7/2012 | Horvath et al. |
| 8,226,712 | B1 | 7/2012 | Frazier et al. |
| 8,790,399 | B2 | 7/2014 | Frazier et al. |
| 2010/0168848 | A1 | 7/2010 | Horvath et al. |
| 2011/0144744 | A1 | 6/2011 | Wampler |
| 2012/0089225 | A1 | 4/2012 | Akkerman et al. |
| 2013/0331934 | A1 | 12/2013 | Kabir et al. |

OTHER PUBLICATIONS

Fox et al., "Total Artificial Hearts—Past, Current, and Future", Journal of Cardiac Surgery, vol. 30, Issue 11, Sep. 2015.

*Primary Examiner* — Brian Dukert
(74) *Attorney, Agent, or Firm* — Howson & Howson LLP (57) ABSTRACT

A total artificial heart for a mammalian cardiovascular system is provided. The total artificial heart has a pump casing including an outer housing and an integral hollow support shaft extending therethrough. The casing defines a first flow path within the outer housing about an exterior of the hollow support shaft and a separate second flow path extending within the hollow support shaft. An annular impeller is housed within the outer housing of the casing for rotation about the hollow support shaft to provide a centrifugal flow pump in the first flow path, and an axial flow impeller is housed within the hollow support shaft of the casing for forming an axial flow pump in the second flow path.

11 Claims, 9 Drawing Sheets

DUAL-PUMP CONTINUOUS-FLOW TOTAL ARTIFICIAL HEART

CROSS REFERENCE TO RELATED APPLICATIONS

This application claims the benefit under 35 USC § 119(e) of U.S. Provisional Patent Application No. 62/127,316, filed Mar. 3, 2015.

BACKGROUND

Congestive heart failure (CHF) is a progressive and debilitating disease that affects an estimated 23 million people worldwide. In the U.S., for instance, approximately 7.5 million people have congestive heart failure (CHF), and more than 670,000 new cases are typically diagnosed each year. The treatment of this volume of patients has been reported as costing the healthcare industry almost $35 billion annually.

Treatment strategies for patients with congestive heart failure typically consist of conventional pharmacologic therapy, which is used for purposes of slowing progression of the disease and to ease symptoms. In advanced stages of the disease, treatment may consist of continuous intravenous inotropic support and subsequent heart transplantation, when qualifications are satisfied and a matched donor heart is located.

While heart transplantation is a viable therapeutic when patients qualify, there is a limited number of donor hearts. For instance, in the U.S. in a given year, over about 3000 patients may be on a waiting list for heart transplants, but only approximately 2200 patients will likely receive a transplant. Accordingly, in excess of 15% of patients on the donor waiting list will likely succumb to the disease due primarily to the lack of a sufficient number of donor hearts. This limitation and the increasing need for biventricular support have necessitated the development of therapeutic alternatives, such as mechanical circulatory support systems, including total artificial hearts (TAHs) and ventricular assist devices (VADs) for use as destination therapy or bridge-to-transplantation.

Blood is in and of itself a tissue with both cellular and fluid components. Cells are suspended in a liquid referred to as plasma. When a blood pump or the like of a TAH or VAD is used to add energy to blood, it is extremely important not to cause damage to red blood cells in particular, which carry oxygen in the body.

TAHs may be designed as pulsatile or continuous flow devices for supporting the systemic and pulmonary circulations. Generally, pulsatile pumps or positive displacement pumps may experience critical failures due to moving parts, namely mechanical valves and flexing membranes. High shear stresses and regions of stagnant flow have led to issues with clot formation inside such devices. Further, high shear stresses as the result of mechanical valves can cause hemolysis where red blood cells are split open releasing hemoglobin. Hemolysis activates platelets in the vicinity leading to thrombus formation or thrombogenesis.

Clinical research appears to indicate that pulsatility in the systemic and pulmonary circulations is not critical for physiologic function. Accordingly, continuous flow pumps with impellers suspended by magnetic bearings are believed to be better able to reduce and prevent regions of stagnant flow and high shear stress through limited contact with the blood. However, thrombus formation or thrombogenesis can occur as the result of poor wash-out of blood contacting surfaces of a TAH leading to stagnant blood that activates platelets causing red blood cells to combine together to form a thrombus. Thus, it is clear that blood cell trauma is a very serious complication of mechanical circulatory devices.

Accordingly, there continues to be a need for the further design and development of TAHs for patients suffering from end stage heart disease. A device designed to reduce complications typically associated with current devices as discussed above and that may be provided as a smaller and more effective TAH capable of suiting a wider patient population may result in the saving of thousands of lives annually. Improvements with respect to biocompatibility of device designs and materials are also desired for purposes of decreasing hemorrhagic and thromboembolic complications, and systems to power implanted driving units, which are fully operational without interruption of skin barriers, are desired to mitigate the risk of infections. Further, a TAH that is more compact and effective for use in smaller adults and children and that have fewer mechanical components to reduce wear and risk of failure is desired.

BRIEF DESCRIPTION OF THE DRAWINGS

Various features of the embodiments described in the following detailed description can be more fully appreciated when considered with reference to the accompanying figures, wherein the same numbers refer to the same elements.

DETAILED DESCRIPTION

For simplicity and illustrative purposes, principles of embodiments are described below by referring primarily to examples thereof. In the following description, numerous specific details are set forth to provide a thorough understanding of the embodiments. It will be apparent to one of ordinary skill in the art that the embodiments may be practiced without limitation to these specific details. In some instances, well known methods and structures have not been described in detail so as not to unnecessarily obscure the embodiments.

Figure 1:
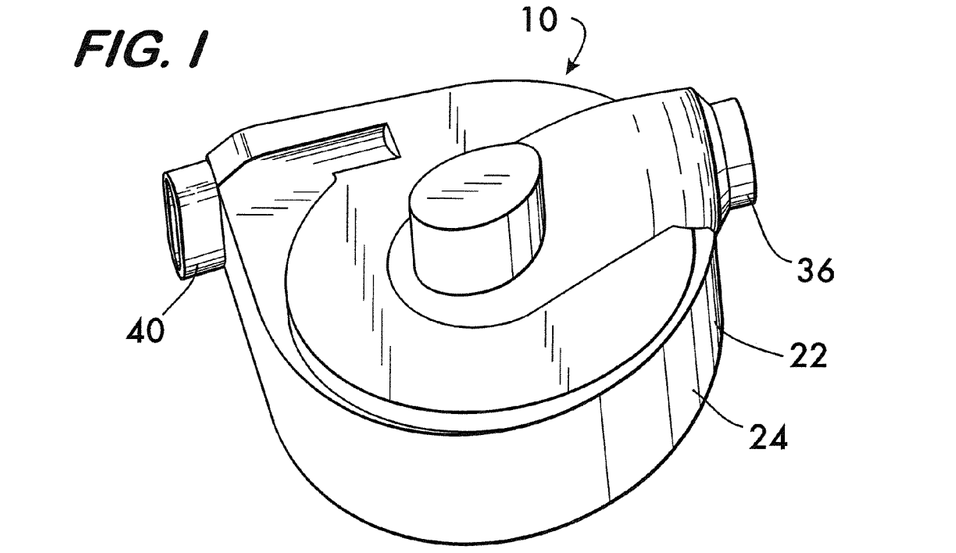
FIG. 1 is a perspective view of a total artificial heart (TAH) in accordance to an embodiment.
Figure 2:
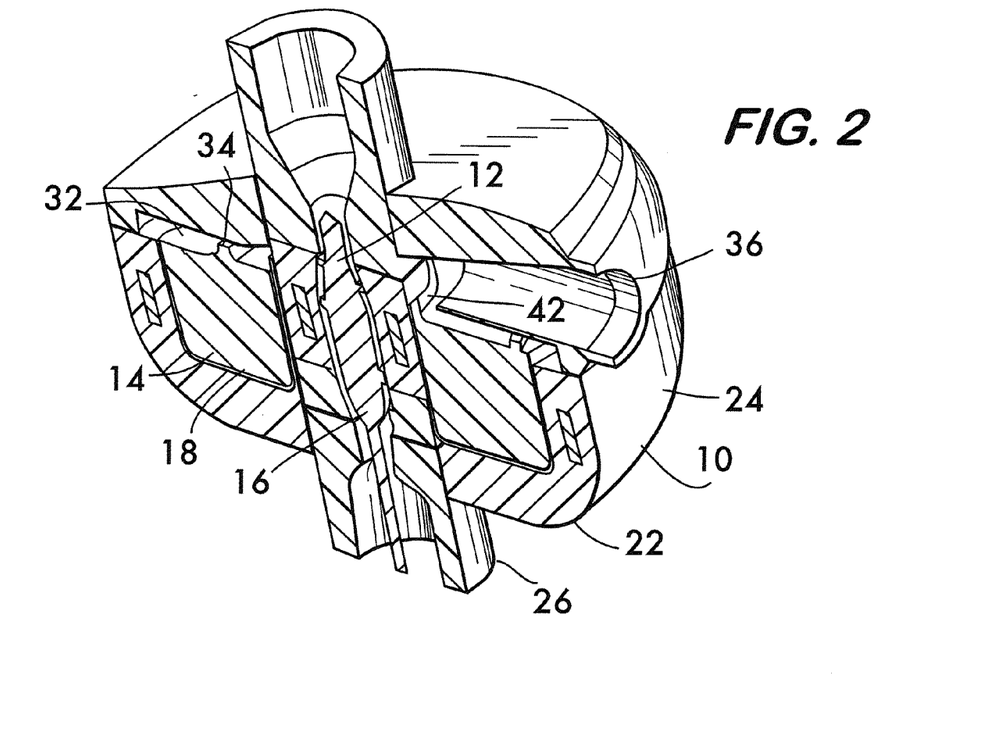
FIG. 2 is a perspective cross-sectional view of the total artificial heart (TAH) of FIG. 1 taken through an axis of rotation of impellers of the TAH in accordance to an embodiment.
Figure 3:
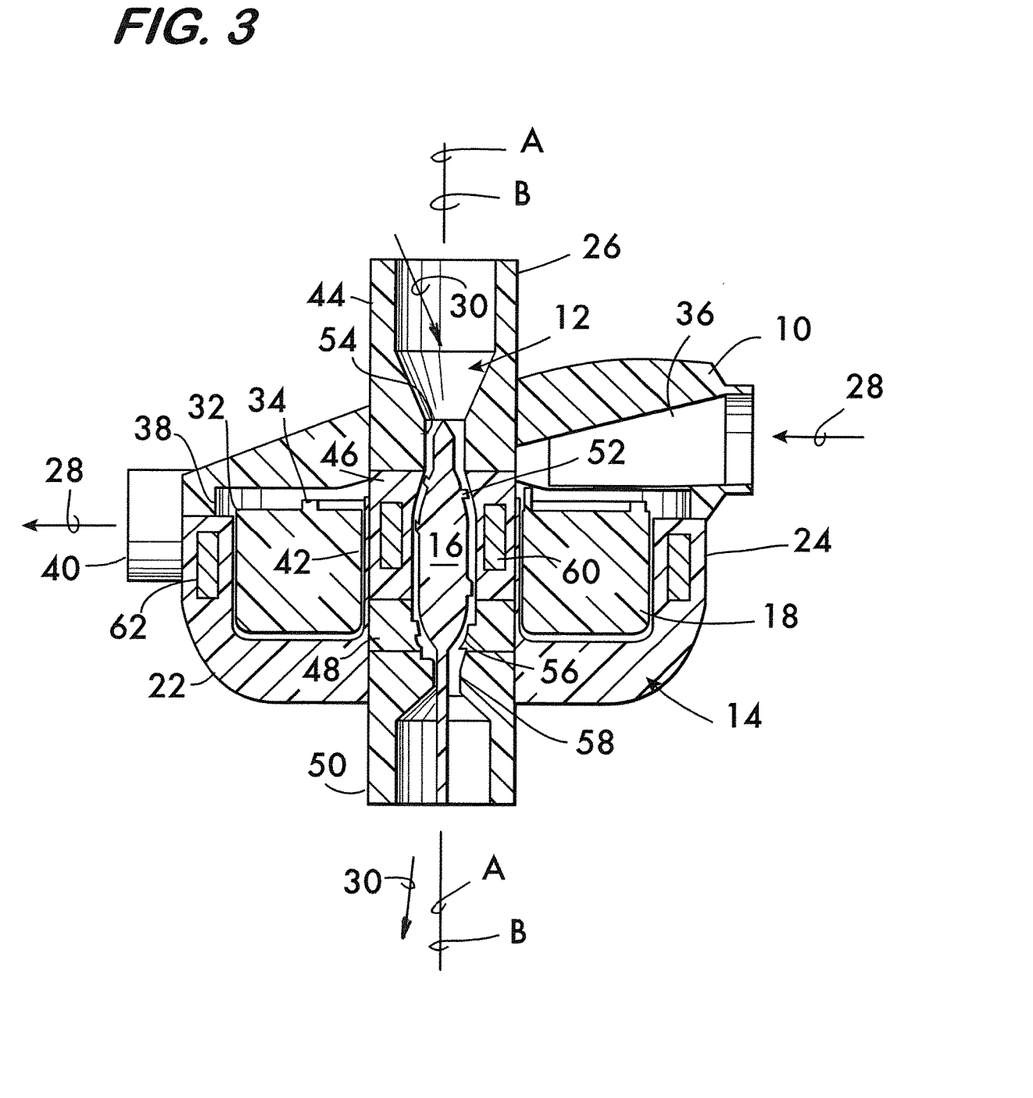
FIG. 3 is a cross-sectional view in elevation of the total artificial heart (TAH) of FIG. 1 taken through a common axis of rotation of impellers of the TAH in accordance to an embodiment.
Figure 4:
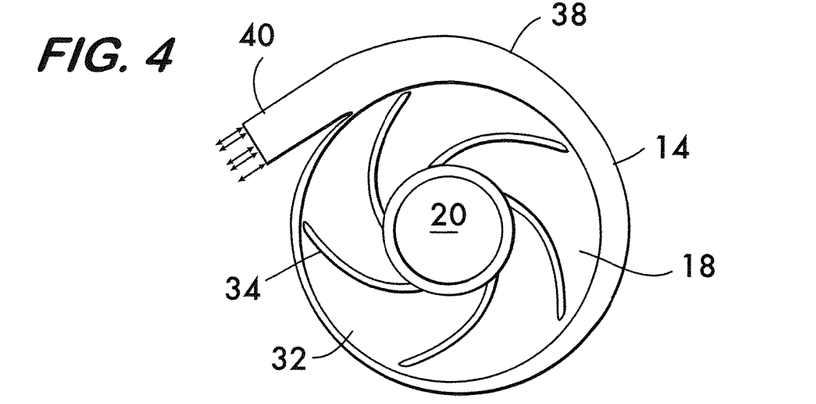
FIG. 4 is a schematic plan view of a centrifugal flow pump of the TAH in accordance to an embodiment.
Figures 5, 6:
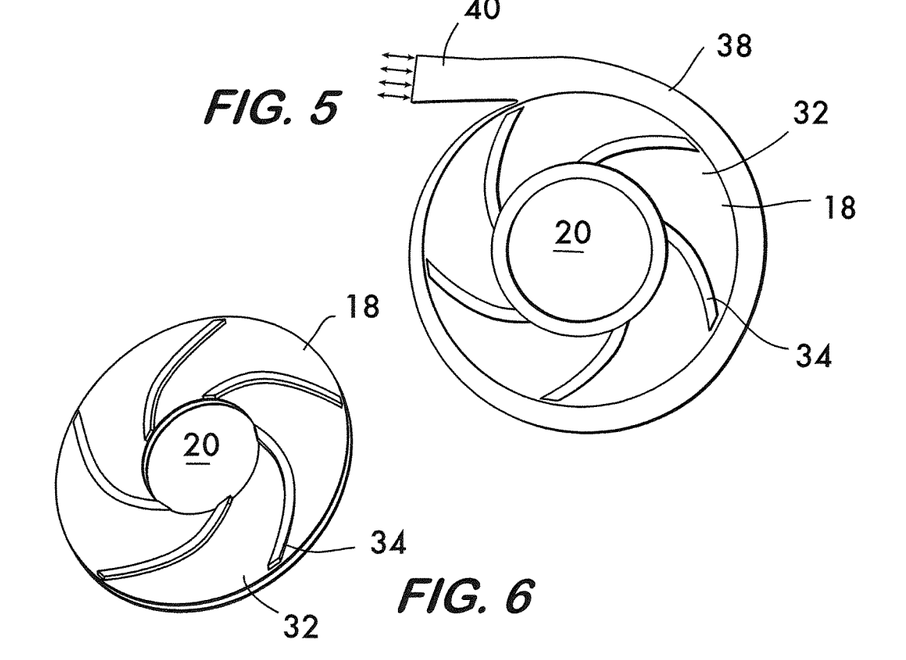
FIG. 5 is a schematic plan view of a centrifugal flow pump of the TAH in accordance to an alternate embodiment.
FIG. 6 is a perspective view of a top surface of an annular impeller of a centrifugal flow pump of the TAH in accordance to an embodiment.

FIGS. 1-3 are directed to an embodiment of a total artificial heart (TAH) 10 which is optimized to address biological restrictions and provide many advantages over current state of the art TAH designs. As described in greater detail below, the TAH 10 combines a pair of pumps, 12 and 14, each having a separate impeller, 16 and 18, uniquely arranged to enable the TAH to be made of a compact size capable of implantation in smaller cavities of patient populations, such as Asian, children, women, and other patients of relatively small frame.

Body surface area (BSA) is a measured or calculated surface area of a human body and has been a problematic design constraint of TAH development. TAH devices have not been available for use in smaller sized patients having relative low BSA due to the size required of the TAH. For instance, clinically available TAHs have conventionally been too large for surgical implantation in patient populations which have a small pericardial cavity. Conventional TAHs have generally required the patient to have a BSA of 1.7 $m^2$ or larger.

According to at least some embodiments, the TAH 10 described herein can be produced at a relative compact size enabling surgical implantation in patients having a BSA as low as or lower than 1.3 $m^2$. For instance, such patient populations include pediatric patients who have varying thoracic cavity sizes due to ongoing growth, persons of Asian descent who may have genetically small thoracic cavities, and some female patients. The TAH 10 can be made at a fraction of the size of conventional TAHs. For this purpose, the TAH 10 utilizes an axial flow blood pump 16 which is arranged to extend directly through an open center 20 of the centrifugal blood flow pump 14 thereby reducing void and unused space in the centrifugal blood flow pump 14. This arrangement of pumps enables a reduction of size of the TAH and enables the TAH to be used in patients having a low BSA.

In addition to being compact, the total artificial heart (TAH) 10 is designed to meet anatomic and physiologic cardiovascular needs of a cardiovascular system. As stated above, the device comprises two different impellers, an axial flow impeller 16 of the axial flow blood pump 12 and an annular centrifugal impeller 18 of the centrifugal flow blood pump 14. This dual pump arrangement is used to provide a mechanical circulatory replacement for diseased human heart physiology by providing two separately controlled continuous flow pumps to circulate blood in the pulmonary and systemic circulations. For instance, the centrifugal flow pump 14 is a continuous flow blood pump designed to circulate blood in a systemic circulation of a mammalian cardiovascular system, and the axial flow pump 12 is a continuous flow blood pump designed to circulate blood in a pulmonary circulation of a mammalian cardiovascular system.

The TAH 10 is designed to be implanted into a pericardial cavity replacing the native ventricles by connecting to the left and right atria or the apex of the left and right ventricles through cannulae. For purposes of example, the operating range for the axial flow blood pump may be 1-7 L/min or 0.5-6 L/min with a pressure generation of 0-30 mmHg or 1-25 mmHg at 3000-10,000 RPM, and the operating range for the centrifugal flow blood pump may be 1-7 L/min or 0.5-6 L/min with a pressure generation of 80-140 mmHg or 70-140 mmHg at 3000-10,000 RPM.

As best shown in FIGS. 2 and 3, the axial flow pump 12 is integrated with the centrifugal flow pump 14 such that the axial flow pump 12 extends through the central opening 20 of the annular impeller 18 of the centrifugal flow pump 14. The TAH 10 includes a pump casing 22 having an outer housing 24 and an integral hollow support shaft 26 extending therethrough. The pump casing 22 defines a first flow path 28 for systemic circulation within the outer housing 24 about an exterior of the hollow support shaft 26 and a separate second flow path 30 for pulmonary circulation extending within the hollow support shaft 26.

The annular impeller 18 of the centrifugal flow pump 14 is housed within the outer housing 24 of the casing 22 and rotates about the hollow support shaft 26 thereby providing the centrifugal flow pump 14 in the first flow path 28 within the TAH 10. As shown in FIGS. 2-6, the annular impeller 18 has a generally ring-shaped body having a central opening 20 and an upper surface 32 with raised vanes 34 for directing the flow of blood in a radial direction during operation and rotation of the annular impeller 18.

For purposes of providing a centrifugal flow pump, the outer housing 24 includes an inlet tube 36 and a volute chamber 38 having a discharge outlet 40. With this arrangement, blood returning from pulmonary circulation is received within the inlet tube 36 and enters the outer housing 24 adjacent an exterior surface 42 of the support shaft 26 with minimal flow disturbance or elevated shear stresses which may cause thrombogenesis. The blood is forced to flow in radial direction by rotation of the annular impeller 18 into the volute chamber 38 where it is collected and discharged via outlet 40 into systemic circulation at a desired pressure and flow rate.

As best shown in FIGS. 1-3, the inlet tube 36 extends adjacent and slightly above the surface 32 of the annular impeller 14 in a radial direction relative to the annular impeller 14. In addition, the inlet tube 36 opens into the outer housing 24 adjacent the exterior surface 32 of the hollow support shaft 26 to feed the blood centrally within the centrifugal flow pump 14. For instance, see FIG. 2. In the illustrated embodiment, flow in the inlet tube 36 and through the outlet 40 of the volute chamber 38 is generally perpendicular to the flow through the hollow support shaft 26. For instance, see FIG. 3. In some embodiments, the inlet tube 36 may be rotatable about the support shaft 26 to enable its positioning to be altered relative to the outlet 40 of the volute chamber 38. In this manner, the relative positioning of the inlet tube 36 and outlet 40 may be optimized for a particular patient.

The axial flow impeller 16 is housed within the hollow support shaft 26 of the pump casing 22 for forming the axial flow pump 12 within the second flow path 30 defined within the support shaft 26. As shown in the illustrated embodiments, the axial flow impeller 16 may be positioned to extend directly within and through the central opening 20 of the annular impeller 18 of the centrifugal flow pump 14. In the illustrated embodiment, an axis of rotation "A" of the centrifugal flow annular impeller 18 may also form and be the same as the axis of rotation "B" of the axial flow impeller 16 (i.e., the impellers 16 and 18 may share a common axis of rotation, see FIG. 3). As an alternative, the axis of rotation "A" and the axis of rotation "B" may be slightly offset, but substantially parallel. As a still further alternative, the axis of rotation "A" may be slightly tilted relative to the axis of rotation "B" such as by an angle of 5° or less.

Figure 7:
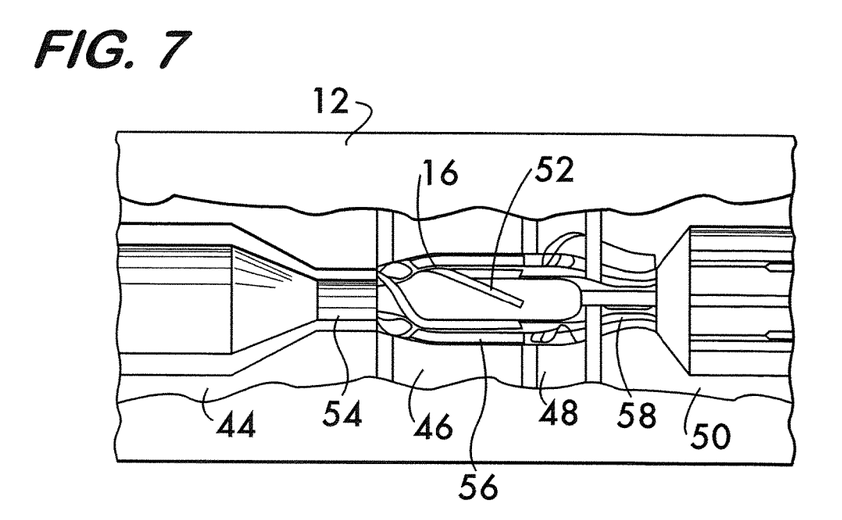
FIG. 7 is a schematic view of the different sections of an axial flow pump of the TAH in accordance to an embodiment.

As best shown in FIG. 7, the second flow path 30 provided by the TAH 10 within the hollow support shaft 26 may include various sections that comprise the axial flow pump 12. For instance, the pump 12 may include an inducer section 44, an impeller housing section 46, a diffuser section 48, and a straightener section 50. The impeller 16 may include blades or vanes 52 providing axial flow of blood through the pump 12 and may be positioned in housing section 46. The inducer section 44 may provide an inlet for blood returning from systemic circulation, may provide a narrowed flow path adjacent the impeller 16, and may include a set of stationary vanes 54 for ensuring axial flow of blood into the impeller housing section 46. The diffuser and straightener sections, 48 and 50, may also include sets of stationary vanes, 56 and 58, for diffusing and straightening flow being discharged into pulmonary circulation at a desired pressure and flow rate.

Figure 8:
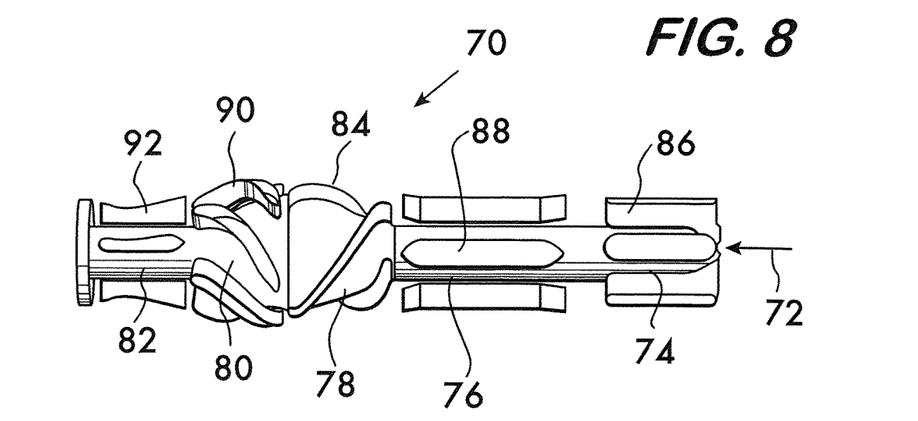
FIG. 8 is a schematic view of the different sections of an axial flow pump of the TAH in accordance to an alternate embodiment.

FIG. 8 provides a slightly alternate arrangement of sections of an axial flow pump 70. The flow path 72 through the pump 70 within a hollow support shaft may include a first inducer section 74, a second inducer section 76, a rotatable impeller 78, a diffuser section 80, and a straightener section 82. The impeller 78 may include blades or vanes 84 providing axial flow of blood through the pump 70. The first inducer section 74 may provide an inlet for blood returning from systemic circulation and may include a set of stationary vanes 86 for ensuring axial flow of blood into the second inducer section 76. The second inducer section 76 may include a set of stationary vanes 88 for further ensuring axial flow of blood provided to the impeller 78. The diffuser and straightener sections, 80 and 82, may also include sets of stationary vanes, 90 and 92, for diffusing and straightening flow being discharged into pulmonary circulation at a desired pressure and flow rate.

The narrow diameter elongate tail piece extending from the impeller 16 as shown in FIG. 3 that extends into the straightener section 50 may be eliminated in its entirety. Instead, the impeller 16 may terminate in the diffuser section 48 in a neck-downed, streamlined section forming a small pointed cone-shaped nose. Impeller 78 shown in FIG. 8 may also be modified as discussed above.

For purposes of levitating or suspending the impellers 16 and 18 and for causing impellers 16 and 18 to rotate, first and second actively controlled and passively placed magnetic bearings 60 and 62 may be carried by the casing 22, such as by being embedded in the walls of the casing 22. Magnetic bearings eliminate problems encountered when using mechanical bearings and fluid seals which have been known to induce hemolysis and thrombogenesis. Also, little to no wear of the impellers, 16 and 18, will be caused by the levitation, and thus the operating lifetime of the TAH 10 is greatly extended, for instance, up to 15 years or longer. Further, the magnetic bearings provide the ability to independently control rotation and operation of the centrifugal impeller 18 and the axial flow impeller 16 while being driven off of a common motor.

By way of example, the axial flow impeller 16 may have a permanent magnet or the like that is electromagnetically coupled to the first magnetic bearings 60, and the annular impeller 18 may have a permanent magnet or the like that is electromagnetically coupled to the second magnetic bearings 62 thereby permitting each impeller to be suspended and rotated at speeds (RPMs) independent of the other impeller. In a contemplated embodiment, each of the first and second magnetic bearings is electrically connected to the same drive motor for powering the bearings. Of course, separate drive motors could be used, if desired. According to one contemplated embodiment, the first magnetic bearings 60 may be located in an inner wall portion forming the hollow support shaft 26 in the housing section 46 of the axial flow pump 12, and the second magnetic bearings 62 may be located in an outer wall portion of the support shaft 26 and/or in an outer wall of the outer housing 24.

The interior blood-contacting surfaces of the casing 22, inlet tube 36, volute chamber 38, outlet 40, and impellers 16 and 18 may be coated with a biopolymer coating such as CARMEDA Biopolymer, Parylene, or MPC. These compounds reduce the risk of thrombogenesis as well suppress any type of biological reaction which may occur. Thus, a patient having the TAH implant may not require the use of cyclosporine or other immunosuppressive drugs as a result of implantation. Another advantage of the TAH 10 is the streamlined flow provided by the first and second flow paths, 28 and 30, through the device. The impeller designs offer streamlined flow patterns that prevent downstream thrombogenesis and break down of blood cells.

Accordingly, the TAH 10 described above is able to provide permanent circulatory support as an alternative to a heart transplant or as bridge to a heart transplant and is of relatively simple construction enabling manufacture of the device with less material and in a compact design. The centrifugal pump is of design that meets critical flow demands of systemic circulation, and the axial flow pump is of a design that meets critical flow demands of pulmonary circulation.

While various dimensions of the TAH 10 may be adjusted as required for a particular patient, an outer diameter of the annular impeller 18 may be 100 mm or less and, more preferably, 70 mm or less. For instance, the outer diameter of the annular impeller 18 may be 70 mm or 50 mm. As a specific example, the outer diameter of the axial flow pump may be 35 mm. As a further example, the length of the support shaft of the axial flow pump may be 50 mm and the outer diameter of the centrifugal flow pump may be 50 mm which may provide a TAH of a size able to be transplanted in patients of BSA less than 1.3 m$^2$.

Figure 9:
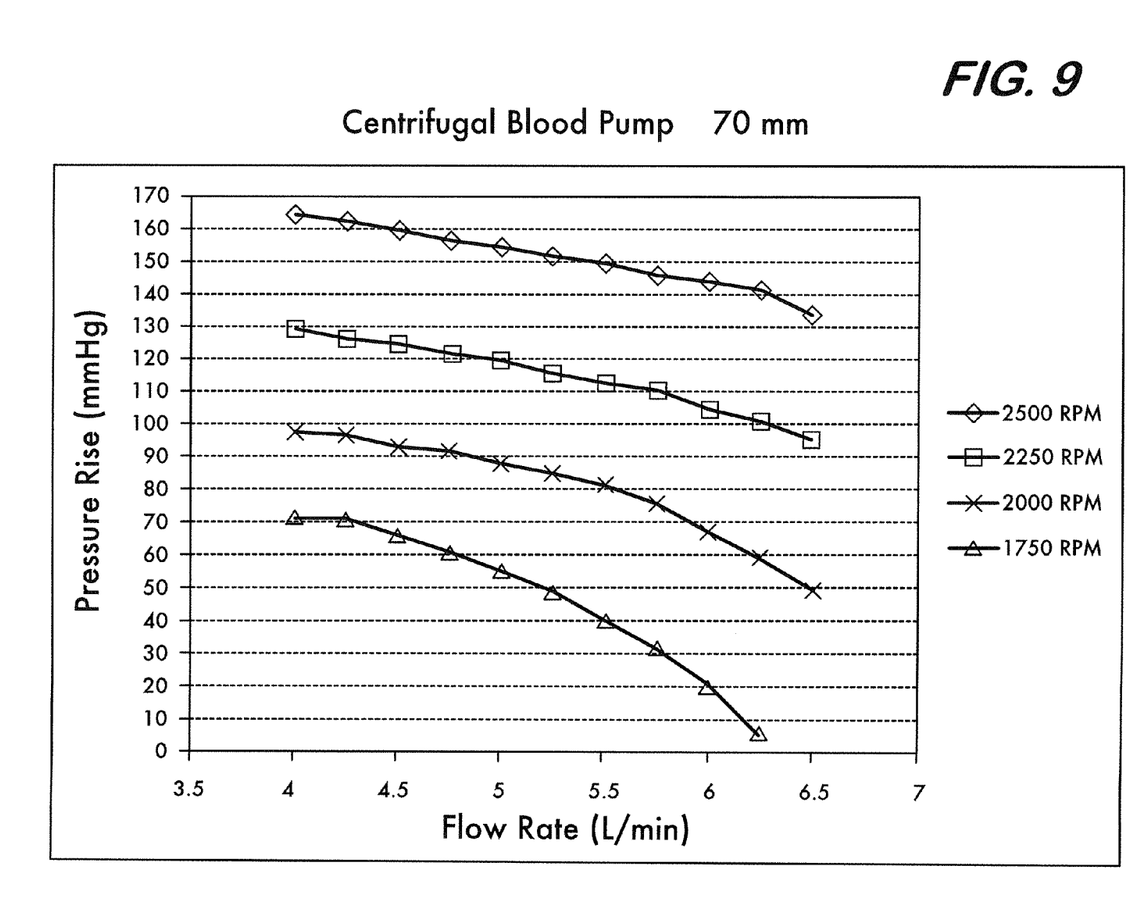
FIG. 9 is a graph illustrating hydraulic performance characteristics of a centrifugal flow blood pump having an outer diameter of 70 mm in accordance to an embodiment.

FIG. 9 provides a graph showing pressure rise (mmHg) versus flow rate (L/min) for an embodiment of the centrifugal flow pump (70 mm outer diameter) measured at rotation speeds of the annular impeller at 1750, 2000, 2250 and 2500 RPMs. The centrifugal flow pump may provide systemic circulation at a flow range of 0.5 to 6 L/min at a pressure of 70 to 140 mmHg with the impeller rotating at between 2,000 to 10,000 RPMs. As shown at the bottom of FIG. 9, 5.5 L/min flow at 80 mmHg pressure was achieved at 2000 RPM of an annular impeller of 70 mm outer diameter.

Figure 10:
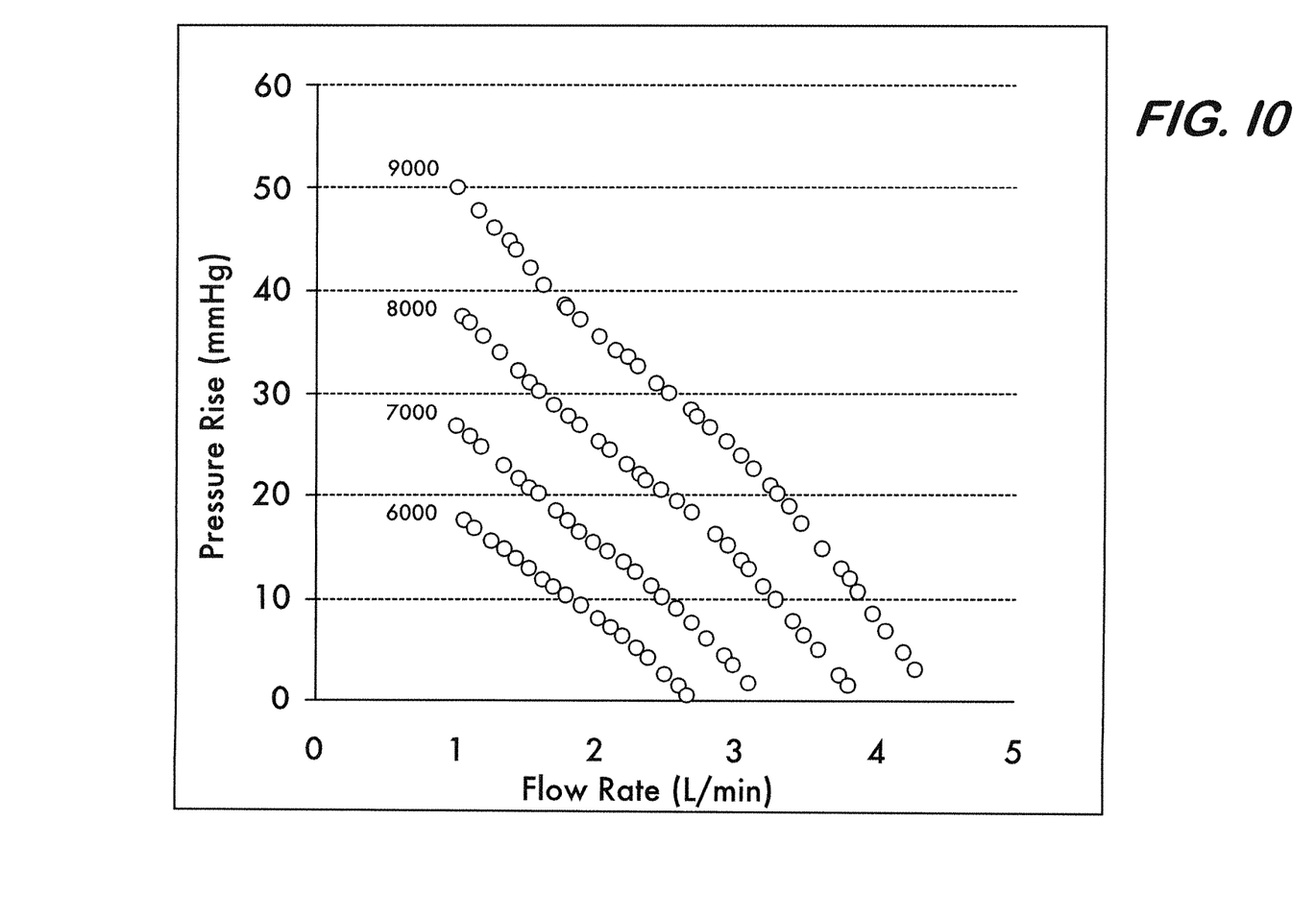
FIG. 10 is a graph illustrating hydraulic performance characteristics of an axial flow blood pump having an outer diameter of 35 mm in accordance to an embodiment.

FIG. 10 provides a graph showing pressure rise (mmHg) versus flow rate (L/min) for an embodiment of the axial flow pump (35 mm outer diameter) measured at rotation speeds of the axial flow impeller at 6000, 7000, 8000 and 9000 RPMs. The axial flow pump may provide pulmonary circulation at a flow range of 0.5 to 6 L/min at a pressure of 1 to 25 mmHg with the impeller rotating at between 3,000 to 10,000 RPMs.

Accordingly, as discussed above, the novel total artificial heart (TAH) 10 may be specifically designed for use in patients with a small body surface area and may incorporate two pumps to provide flow to the pulmonary and the systemic circulations. The TAH 10 contains an axial-flow pump to pump blood in the pulmonary circulation and a centrifugal pump to pump blood in the systemic circulation. In addition, for patients that may have poor oxygenation, an oxygenation unit may be incorporated into the TAH 10 to provide further support for pulmonary circulation. The oxygenator may be connected to the TAH 10 as either a combined component with a direct connection to the axial flow pump or as a separate unit connected to the axial flow pump using a PTFE graft or cannula. Thus, the oxygenator is designed to be implantable and to provide assisted oxygenation of the blood for the lungs.

Figure 11:
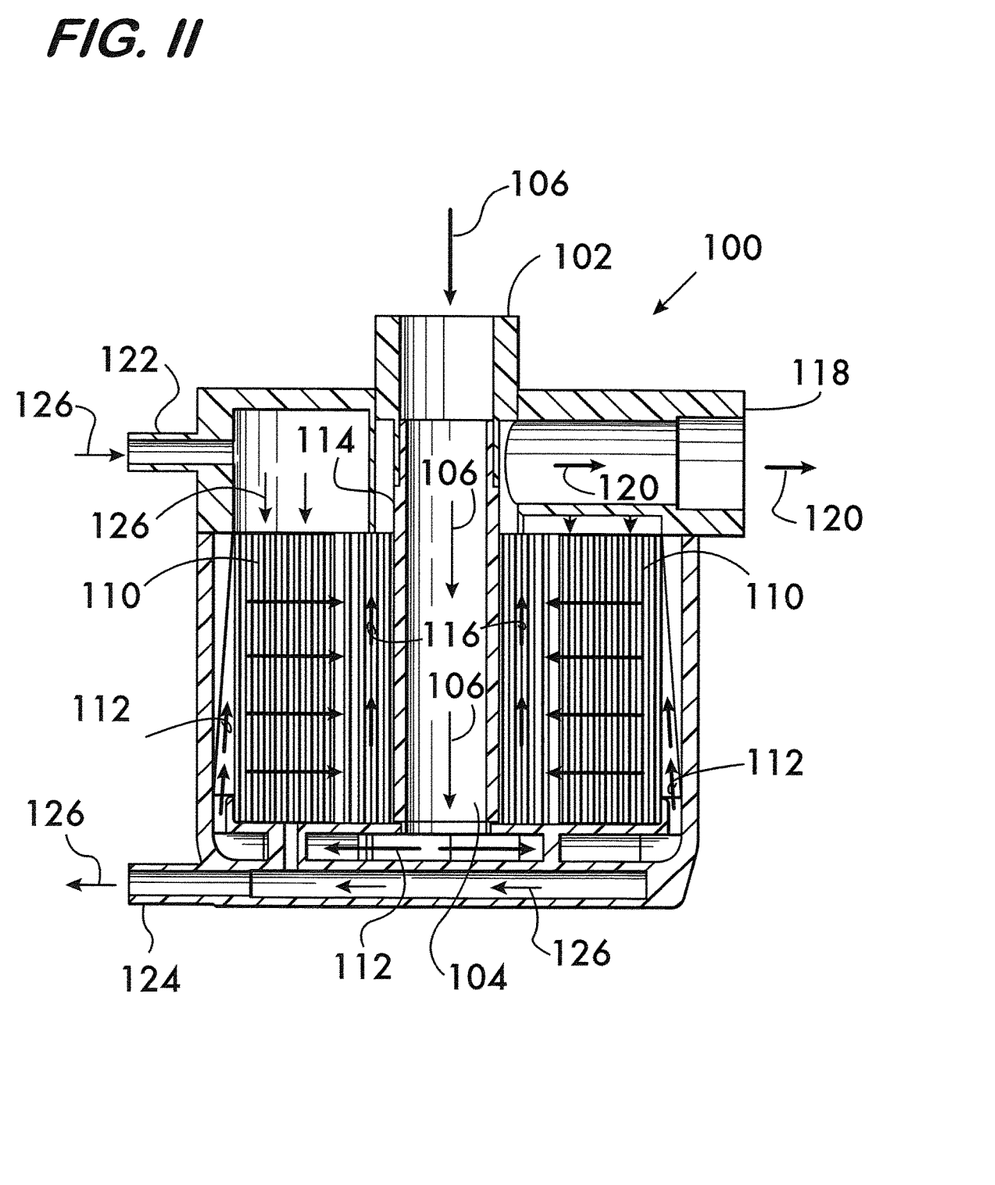
FIG. 11 is a cross-sectional view of an oxygenation unit for a total artificial heart (TAH) in accordance to an embodiment.

An oxygenation unit, or oxygenator, 100 is shown in FIG. 11. The oxygenation unit 100 includes an inlet 102 for blood flow through a central channel 104. See arrows 106 showing blood flow into the inlet 102 and through the central channel 104. At an end 108 of the oxygenation unit 100 opposite the inlet 102, blood flow is directed radially outward from the central channel 104 to an outside of oxygenation tubules 110. See arrows 112 showing blood flow adjacent the end 108 and into the oxygenation tubules 110. The blood picks up oxygen as it travels through the oxygenation tubules 110 and then travels upward along an exterior wall 114 defining the central channel 104. See arrows 116 showing blood flow through the oxygenation tubules and along the wall 114. The blood flow then exits an outlet 118 of the oxygenation unit 110. See arrows 120.

The oxygenation unit 110 also includes an inlet 122 for $O_2$ gas and an outlet 124 for $O_2$ and $CO_2$ gas. Arrows 126 show the path of the gas into the inlet 122, through the oxygenation tubules 110 and then to outlet 124.

The oxygenation tubules 110 include microchannels to permit oxygen transport to occur using micropores. This construction eliminates problems associated with gas bubbling, blood bubbling, and blood foaming and enhances gas exchange to the red blood cells by providing oxygen and removing carbon dioxide. The use of microchannels allows for decreased resistance to blood flow to increase gas transport efficiency and biocompatibility. Oxygen is supplied to the oxygenator via a supply tube and carbon dioxide is removed through an exhaust tube. The tubes may be connected to an external gas supply module worn by the patient that is able to remove oxygen from room air using an oxygen concentrator or an oxygen separator. Accordingly, use of the oxygenation unit 100 limits the requirement for a stream of pure oxygen used in conventional oxygenator designs.

Figure 12:
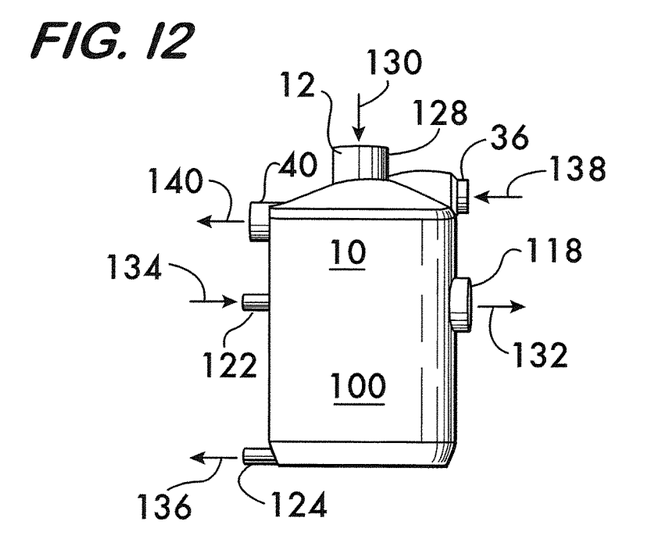
FIG. 12 is an elevational view of a total artificial heart (TAH) with oxygenation unit in accordance to an embodiment.

FIG. 12 shows an embodiment in which an oxygenation unit 100 is directly connected to and integrated with the axial-flow pump 12 of the TAH 10 discussed above. Blood flows into the TAH 10 through inlet 128 (see arrow 130) and through the axial-flow pump of the TAH 10 as described above. Blood then flows into the inlet of the oxygenation unit 100 where it picks up oxygen and exits the oxygenation unit 100 at outlet 118 (see arrow 132). Oxygen ($O_2$) flows into the gas inlet 122 of the oxygenation unit 100 (see arrow 134) and $O_2$ and $CO_2$ gas exits through an outlet 124 (see arrow 136) as described above. In addition, blood also flows through the centrifugal pump of the TAH 10 by entering through inlet 36 (see arrow 138) and exiting through outlet 40 (see arrow 140) as described above.

Figure 13:
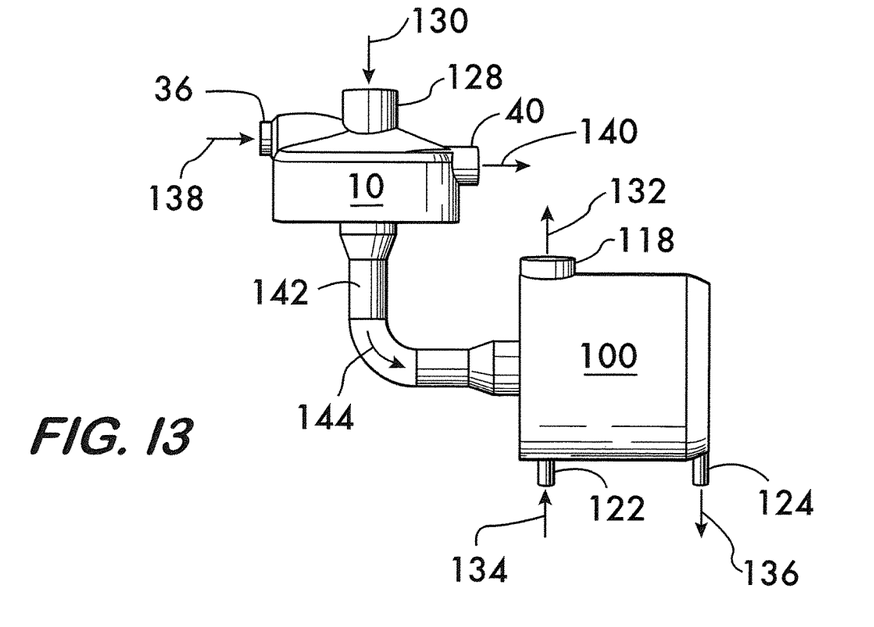
FIG. 13 is an elevational view of a total artificial heart (TAH) with oxygenation unit in accordance to an alternate embodiment.

FIG. 13 shows the oxygenation unit 100 connected with a graft 142 to the axial-flow pump of the TAH 10 in an alternate configuration. In this embodiment, blood flows into the TAH 10 through inlet 128 (see arrow 130) and through the axial-flow pump of the TAH 10 and into graft 142 (see arrow 144) as described above. Blood then flows into the inlet of the oxygenation unit 100 where it picks up oxygen and exits the oxygenation unit 100 at outlet 118 (see arrow 132). Oxygen ($O_2$) flows into the gas inlet 122 of the oxygenation unit 100 (see arrow 134) and $O_2$ and $CO_2$ gas exits through an outlet 124 (see arrow 136) as described above. In addition, blood also flows through the centrifugal pump of the TAH 10 by entering through inlet 36 (see arrow 138) and exiting through outlet 40 (see arrow 140) as described above.

Figure 14:
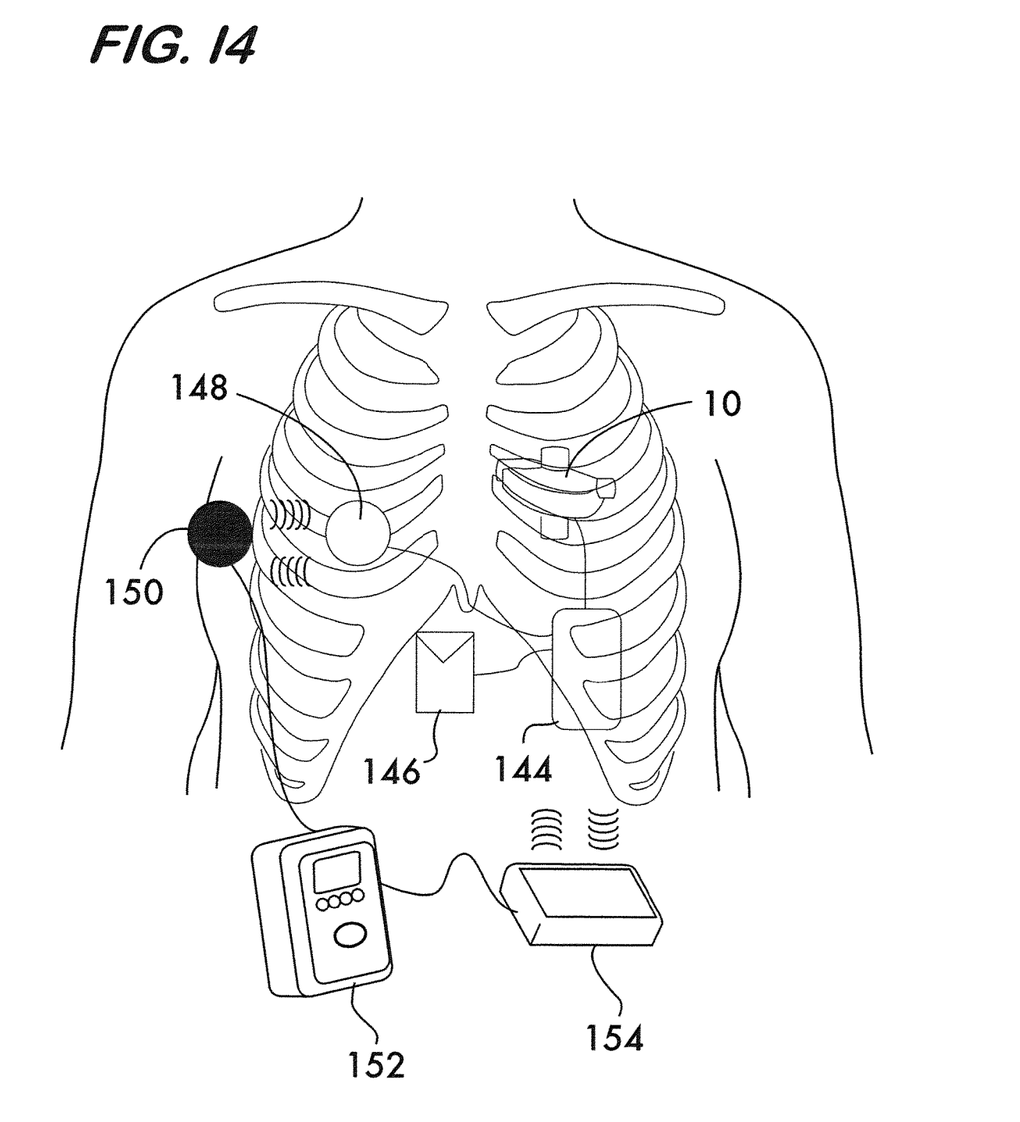
FIG. 14 is a schematic view of an implant configuration of a total artificial heart (TAH) in accordance to an embodiment.

Finally, as shown in FIG. 14, the TAH 10 may incorporate wireless technologies to make the device completely intracorporeal, thereby removing the risk of infections from percutaneous power and drive lines exiting through the abdomen. Thus, power may be supplied to the internal components (i.e., the TAH 10, an implanted controller 144 with implanted battery 146, and implanted energy transfer device 148 without breaking the skin via an external energy transfer device 150. A WiFi or Bluetooth system may be applied to provide control signals from an external controller 152 and RF communication module 154 to request and receive reports of operational status to and from the TAH 10.

The TAH 10 may be designed with lighter materials to reduce the weight of components such as the batteries and controllers. The TAH 10 may have an overall size of about 60 mm×50 mm, produce pressures and flows necessary for CHF patients. For instance, the TAH 10 may generate 3-6 L/min of flow with a pressure of 15-25 mmHg for the pulmonary circulation and 80-140 mmHg for the systemic circulation at speeds of 2,000-15,000 RPM. By ramping speed, the TAH 10 has the capability to provide both pulsatile and continuous flow support without the use of valves or membranes.

While the principles of the invention have been described above in connection with specific devices, systems, and/or methods, it is to be clearly understood that this description is made only by way of example and not as limitation. For instance, while a TAH is described above, the disclosed device may be used in any mechanical circulatory support system, such as a ventricular assist device (VAD) or the like. In addition, the pump design may also be used for other medical and non-medical purposes.

One of ordinary skill in the art will appreciate that various modifications and changes can be made without departing from the scope of the claims below. Accordingly, the specification and figures are to be regarded in an illustrative rather than a restrictive sense, and all such modifications are intended to be included within the scope of the present invention.

We claim:

1. A total artificial heart for a mammalian cardiovascular system, comprising:
   a casing including an outer housing and an integral hollow support shaft extending therethrough, said casing defining a first flow path within the outer housing about an exterior of said hollow support shaft and a separate second flow path extending within said hollow support shaft;

an annular impeller housed within said outer housing of said casing for rotation about said hollow support shaft to provide a centrifugal flow pump in said first flow path; and an axial flow impeller housed within said hollow support shaft of said casing for forming an axial flow pump in said second flow path.

2. A total artificial heart according to claim 1, wherein said axial flow impeller of said axial flow pump extends within a central opening of said annular impeller of said centrifugal flow pump within said casing.

3. A total artificial heart according to claim 1, wherein an axis of rotation of said annular impeller of said centrifugal flow pump within said casing is parallel or tilted at an angle of less than about 5° to an axis of rotation of said axial flow impeller of said axial flow pump within said casing.

4. A total artificial heart according to claim 1, wherein said annular impeller of said centrifugal flow pump and said axial flow impeller of said axial flow pump each rotate about a common axis of rotation within said casing.

5. A total artificial heart according to claim 1, wherein said centrifugal flow pump is a continuous flow blood pump for circulating blood in a systemic circulation of a mammalian cardiovascular system, and wherein said axial flow pump is a continuous flow blood pump for circulating blood in a pulmonary circulation of the mammalian cardiovascular system.

6. A total artificial heart according to claim 1, further comprising first and second magnetic bearings embedded within walls forming said casing, wherein said annular impeller is electromagnetically coupled to said first magnetic bearings for independently suspending and controlling rotation of said annular impeller within said outer housing of said casing, and wherein said axial flow impeller is electromagnetically coupled to said second magnetic bearings for independently suspending and controlling rotation of said axial flow impeller within said hollow support shaft of said casing.

7. A total artificial heart according to claim 6, further comprising a drive motor electrically connected to said first and second magnetic bearings.

8. A total artificial heart according to claim 1, wherein said outer housing includes an inlet tube and a volute chamber with an outlet defining parts of said first flow path, and wherein said inlet tube extends adjacent and in a radial direction relative to said annular impeller and opens into said outer housing adjacent an exterior surface of said hollow support shaft.

9. A total artificial heart according to claim 1, wherein said second flow path includes at least one set of stationary vanes for inducing, diffusing, or straightening flow through said axial flow pump, and wherein surfaces of said first and second flow paths and said axial flow and annular impellers have a biopolymer coating that reduces risk of thrombogenesis and suppresses biological reaction.

10. A total artificial heart according to claim 5, further comprising an oxygenation unit such that blood flow exiting said axial flow pump is directed into an inlet of the oxygenation unit and passes through oxygenation tubules in said oxygenation unit to cause oxygen transfer to the blood.

11. A total artificial heart according to claim 10, wherein said oxygenation unit includes an inlet for receiving blood flow from said axial flow pump, an outlet for oxygenated blood, a gas inlet for oxygen supplied to the oxygenation tubules, and a gas outlet for oxygen and carbon dioxide exiting the oxygenation unit.

* * * * *